US009983152B1

(12) United States Patent
Randolph et al.

(10) Patent No.: US 9,983,152 B1
(45) Date of Patent: May 29, 2018

(54) MATERIAL CHARACTERIZATION USING ION CHANNELING IMAGING

(71) Applicant: FEI Company, Hillsboro, OR (US)

(72) Inventors: Steven Randolph, Portland, OR (US); Chad Rue, Portland, OR (US)

(73) Assignee: FEI Company, Hillsboro, OR (US)

( * ) Notice: Subject to any disclaimer, the term of this patent is extended or adjusted under 35 U.S.C. 154(b) by 0 days. days.

(21) Appl. No.: 15/354,972

(22) Filed: Nov. 17, 2016

(51) Int. Cl.
  *G01N 23/22* (2018.01)
  *G01N 23/207* (2018.01)
  *G01N 23/225* (2018.01)

(52) U.S. Cl.
  CPC ..... *G01N 23/2076* (2013.01); *G01N 23/2257* (2013.01)

(58) Field of Classification Search
  CPC ........... G01N 23/2076; G01N 23/2257; G01N 23/02; G01N 23/225; G01N 23/2255; G23N 23/04; H01J 37/026; H01J 37/04; H01J 37/08; H01J 37/28; H01J 37/3005
  USPC ................... 250/306, 307, 309, 492.1, 492.3
  See application file for complete search history.

(56) References Cited

U.S. PATENT DOCUMENTS

| 2005/0103995 | A1* | 5/2005 | Yanagiuchi | G01N 23/225 250/309 |
| 2006/0231752 | A1* | 10/2006 | Houge | H01J 37/295 250/306 |
| 2009/0179161 | A1* | 7/2009 | Ward | B82Y 10/00 250/492.21 |
| 2013/0015351 | A1 | 1/2013 | Kooijman et al. | |
| 2016/0322194 | A1 | 11/2016 | Kooijman et al. | |

OTHER PUBLICATIONS

Davut, K & Zaefferer, S. "Improving the Reliability of EBSD-based Texture Analysis by a New Large Area Mapping Technique", Materials Science Forum, Dec. 2011, pp. 566-569, vol. 702-703.

(Continued)

*Primary Examiner* — Nicole Ippolito
(74) *Attorney, Agent, or Firm* — Scheinberg & Associates, PC; Michael O. Scheinberg (57) ABSTRACT

A system and method of characterizing a work piece, comprising:
  scanning an ion beam across an exposed surface of a work piece, the ion beam causing the emission of secondary electrons at multiple imaging points of the scan, the number of secondary electrons emitted varying at different ones of the multiple imaging points;
  detecting the emitted secondary electrons at each of the multiple imaging point to form an image, the brightness of each point in the image being determined by the number of secondary electrons detected at a corresponding imaging point on the work piece;
  determining grain boundaries in the work piece using the differences in brightness at different points in the image, the grain boundaries defining multiple grains;
  directing a charged particle beam toward one or more analysis points within one or more of the grains, the number of the one or more analysis points within each grain being less than the number of imaging points within the same grain; and
  detecting emissions from the work piece sample at each analysis point;
and determining the composition or crystal structure of one or more grains based on the detected secondary emissions.

16 Claims, 6 Drawing Sheets

(56) References Cited

OTHER PUBLICATIONS

Fibics, "Grain Orientation Contrast," Retrieved from the Internet Apr. 3, 2017; http://www.fibics.com/fib/tutorials/grain-orientation-contrast/6/, 1 page.

Gutierrez-Urrutia, I., et al. "Coupling of Electron Channeling with EBSD: Toward the Quantitative Characterization of Deformation Structures in the SEM", The Journal of the Minerals, Metals & Materials Society, Jul. 16, 2013, pp. 1229-1236, vol. 65 No. 9, 2013 TMS.

* cited by examiner

MATERIAL CHARACTERIZATION USING ION CHANNELING IMAGING

TECHNICAL FIELD OF THE INVENTION

The present invention relates to material characterization of a sample using high resolution ion channeling imaging.

BACKGROUND OF THE INVENTION

Samples, such as mineral samples and other work pieces, are analyzed using a variety of different techniques. In electron backscatter diffraction (EBSD), an electron beam dwells at a point on the work piece surface. Electrons that are backscattered near the surface are diffracted after scattering off crystal planes in the sample. The backscattered electrons are detected to form an image of a diffraction pattern. The diffraction pattern can be indexed and used to identify the crystal structure of the work piece at the dwell point. From the diffraction pattern, the crystal structure of the work piece at the dwell point can be determined. When an investigator has some idea of the materials that make up the work piece, the investigator can match the crystal structure determined by EBSD with the known crystal structures of the expected materials to determine the material's structure, phase, and/or composition at the dwell point.

Another technique for determining the composition at a dwell point is x-ray spectroscopy, including wavelength dispersive x-ray spectroscopy (WDS) and energy dispersive x-ray spectroscopy (EDS). In these method an electron beam is directed toward a sample and excites inner shell electrons of the sample. The decay from the excited state back to a lower energy state yields an x-ray with a energy/wavelength characteristic of the atom from which it was emitted. In EDS, the energies of x-rays coming from the sample in response to the electron beam are measured and plotted in a histogram to form a spectrum. The measured spectrum can be compared to the known spectra of various elements to determine which elements and minerals are present. Alternatively, the relative number of x-rays within specific frequency ranges or channels are compared to the relative number of x-rays within those same frequency ranges in reference materials to identify the material at the dwell point.

EDS can be used to determine the materials present in a work piece and then the crystal structures of the known materials can be compared to the crystal structure at individual dwell points as determined by EBSD or other techniques.

To map a surface by EDS or EBSD is time consuming. These techniques require relatively long dwell times at each dwell point to achieve good signal-to-noise ratios for obtaining high resolution grain and/or compositional images of the sample. To measure sufficient points to obtain a high resolution surface mapping requires measuring many dwell points that are close together. Obtaining sufficient x-rays for an individual dwell point can take 1 or 10 milliseconds. For an image of one thousand by one thousand pixels, obtaining the compositional information from the x-ray detector can take from about fifteen minutes to a few hours.

In a process known as "slice-and-view," a three-dimensional image can be obtained by repetitively mapping a succession of two-dimensional surfaces, repetitively removing a thin slice to expose a new surface, and then mapping the newly exposed surface. The multiple two-dimensional maps are then mathematically combined to reconstruct a three-dimensional representation. The thin slices can be removed, for example, by a focused ion beam, a laser beam, or a microtome. The thickness of the thin slice can be between the order of nanometers, 10s of nanometers, 100s of nanometers or microns depending upon the slicing method and desired resolution. A laser allows a large volume to be removed with each slice resulting in a much larger surface area or "face" to be analyzed. The large surface area increases the time to map each surface, rendering high resolution mapping by EDS or EBSD impractically slow. For example, a slice-and-view surface prepared by FIB, plasma FIB, or laser may have an area greater than 5×5 microns square, greater than 50×50 microns square, or even greater than 1,000×1,000 microns square.

The surface can be mapped more quickly by measuring fewer dwell point by spacing the dwell points further apart or by reducing the dwell time, but the resulting image is coarse or fuzzy because insufficient data is acquired to produce a high resolution image.

The MLA Automated Mineral Analysis System from FEI Company, the assignor of the present invention, can operate in a rapid acquisition mode. An image is first acquired using a backscattered electron detector. The image is then processed to identify regions that appear from the contrast to have the same elemental composition. The beam is then positioned at the centroid of each identified region for a longer dwell time to collect an x-ray spectrum representative of the region. Similarly, U.S. Pat. Pub. 20130015351 to Kooijman et al, for "Clustering of Multi-Modal Data" describes directing an electron beam toward a work piece to determine grain boundaries and then combining x-ray data from points inside each grain to compile an x-ray spectrum.

Backscattering of electrons depends on the atomic number of the elements in the surface and upon the geometric relationship between the surface, the primary beam, and the detector. The backscattered electron image therefore shows boundaries between regions of composed of materials having different average atomic numbers and regions separate by topographical feature. Grains composed of the same or similar materials but having different crystal orientation may therefore be indistinguishable in a backscatter electron image. Grains composed of materials having similar average atomic numbers may also be difficult to identify.

Figure 1A:
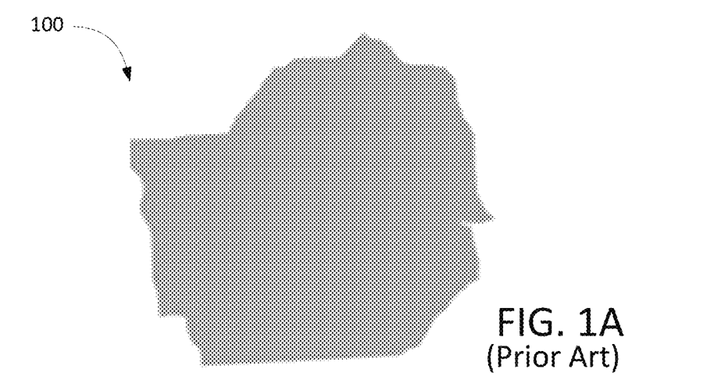
FIG. 1A, FIG. 1B and FIG. 1C illustrate a prior art method of obtaining an EBSD grain image of a sample.
Figure 1B:
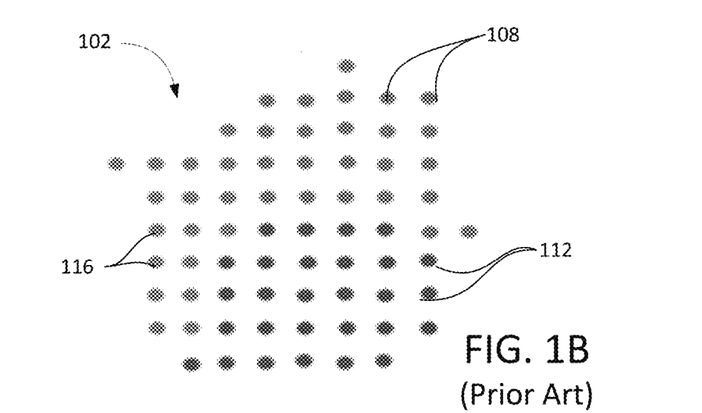
Figure 1C:
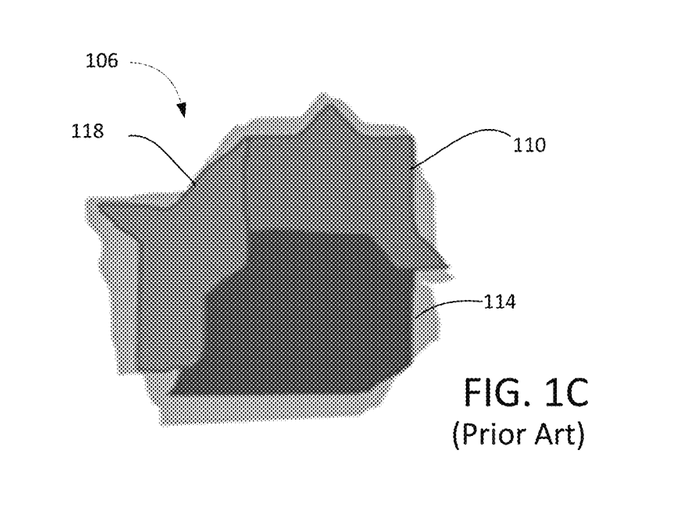

FIGS. 1A-1C illustrate an EBSD mapping process. FIG. 1A shows a scanning electron microscope image 100 of a surface of a work piece. The surface may be, for example, the top surface of a polished mineral sample or a sample surface exposed by a FIB or laser slicing off a layer of the work piece. FIG. 1B shows an EBSD map 102 of the region shown in FIG. 1A. Dwell points represented by the same color indicate diffraction patterns showing similar characteristics. For example, all blue dwell points 108 represent the same first grain orientation, all red dwell points 112 represent the same second grain orientation, and all green dwell points 116 represent the same third grain orientation. Because each dwell point requires a relatively long time to obtain an EBSD image, fewer dwell points can be used in practice, so the dwell points of the EBSD map are relatively far apart. FIG. 1C shows the relatively low resolution grain orientation map 106 that results from the dwell points of FIG. 1B, with region 110 being defined by the dwell points 108, region 114 being defined by the dwell points 112, and region 118 defined by dwell points 116. Note how the map does not follow the contour of the electron microscope image exactly. The grain boundaries are similarly inexact.

When an ion beam is directed toward a work piece, the ions in the beam may be channeled into a crystal to varying degrees depending upon the angle that the ions make with the crystal planes. The number of secondary electrons emitted sufficiently close to the surface and available to be detected will vary with whether the ions are stopped near the surface or whether they channel deeper into the work piece. Secondary electrons created below the work piece surface are reabsorbed in the sample and are unlikely to escape the sample to be detected. Thus, crystal grains having different crystal orientations may show different gray levels on a scanning ion microscopy (SIM) image because the ion channeling depends on the orientation of the crystal planes relative to the beam. The term "ion channeling image" is used to mean a SIM image formed using the number of secondary electrons collected at each dwell point of the focused ino beam.

Using an ion beam for imaging and analysis has several disadvantages. The resolution of a SIM image is typically worse than the resolution of a scanning electron microscope (SEM) image. The mass of the ions will inevitably result in some damage to the sample. While a lower beam energy reduces the sample damage, the lower beam energy slows ions, providing more time for the ions in the beam to repel each other and spread out the beam, reducing resolution. Also, the ions implanted into the work piece can affect some of the properties of the work piece.

Another technique for determining crystal plane orientation entails directing an ion beam toward the work piece at different angles, and recording the number of secondary electrons (which correspond to the brightness of the SIM image) emitted at various angles. The relationship between the angle and the number of secondary electrons detected can be used to calculate the spacing of the crystal planes. Such a technique is described, for example, in Fibics Incorporated Tutorial, "Grain Orientation Contrast" as seen at www.fibics.com/fib/tutorials/grain-orientation-contrast/6/, which is hereby incorporated by reference.

SUMMARY OF THE INVENTION

An object of the invention is to provide a method and apparatus for mapping crystal grain properties more rapidly and/or at higher resolution.

An ion channeling image can be obtained that delineates grain boundaries. After the grain boundaries are determined, properties of individuals grains can be determined by analyzing points within individual grains.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

An ion channeling image of a sample is acquired to determine boundaries of individual grains in the work piece. Because an ion channeling image can be acquired rapidly with relatively short dwell times at each point, the dwell points can be close together to rapidly acquire a high resolution image defining the grain boundaries. The orientation of crystal planes relative to the work piece surface typically varies from grain to grain. An ion channeling image is sensitive to changes in crystal orientation and makes visible boundaries between grains of the same material having different crystal orientations. An ion beam image is more sensitive to crystal orientation because electrons react primarily with electron cloud in the surface atoms, whereas ions react primarily with the nuclei, which are more localized in the orderly structure of the crystal. Moreover, as the ion mill rate of the most materials varies with the crystal orientation, grains having different oreintations will etch at slightly different rates, leaving a topographical feature at the grain boundary that further delineates grain boundaries. The contrast between grain boundaries from ion channeling varies with the material comprising the grain and the ion species. For example, copper and platinum show very good channeling contrast, and gallium and xenon ions have shown good channeling contrast on some materials.

After the grain boundaries are identified, EBSD or EDS can be performed on a relatively few points within each grain to acquire information about the crystal structure (EBSD) or composition (EDS) of the grain. Using an ion channeling image to define the grain boundaries reduces the number of dwell points at which it is necessary to acquire EBSD or EDS information because the EBSD and EDS images are not used to define the edge of the grains.

Alternatively, information about the crystal structure can be determined by acquiring multiple ion channeling images at different angles between the ion beam and the work piece surface, a technique that will be referred to as "spin indexing." For example, when the ion beam is oriented parallel to major crystal planes, the ions will tend to channel deeper below the surface, and secondary electrons generated below the work piece will not escape the work piece and be detected. Points on the image will therefore appear darker than when the ions impinge at an angle to the major crystal planes and are stopped nearer the surface, generating secondary electrons at or near the surface.

As shown in Fibics Incorporated Tutorial, "Grain Orientation Contrast" mentioned above, a graph of gray level versus tilt angle of the ion beam can be approximately sinusoidal. In spin indexing, because the acquisition of an ion channeling image is relatively quick, the number of dwell points in the scan at each angle can be the same as, or less than, the number of dwell points in the original scan used to determine the grain boundaries. Thus, the entire portion of the work piece can be scanned multiple times at the same resolution as that used to determine the grain boundary, or the scan resolution can be lower, that is, dwell points fewer and further apart, because the grain boundaries are already determined. The initial scan that was used to determine the grain boundaries can also be used as a data point in the spin indexing series.

The techniques described herein can be used on a single surface, or can be applied to the work piece multiple times with a "slice-and-view" technique that exposes a succession of surfaces by removing layers from the work piece surface. The succession of two-dimensional images provides data to reconstruct a three-dimensional representation of the work piece.

Figure 2:
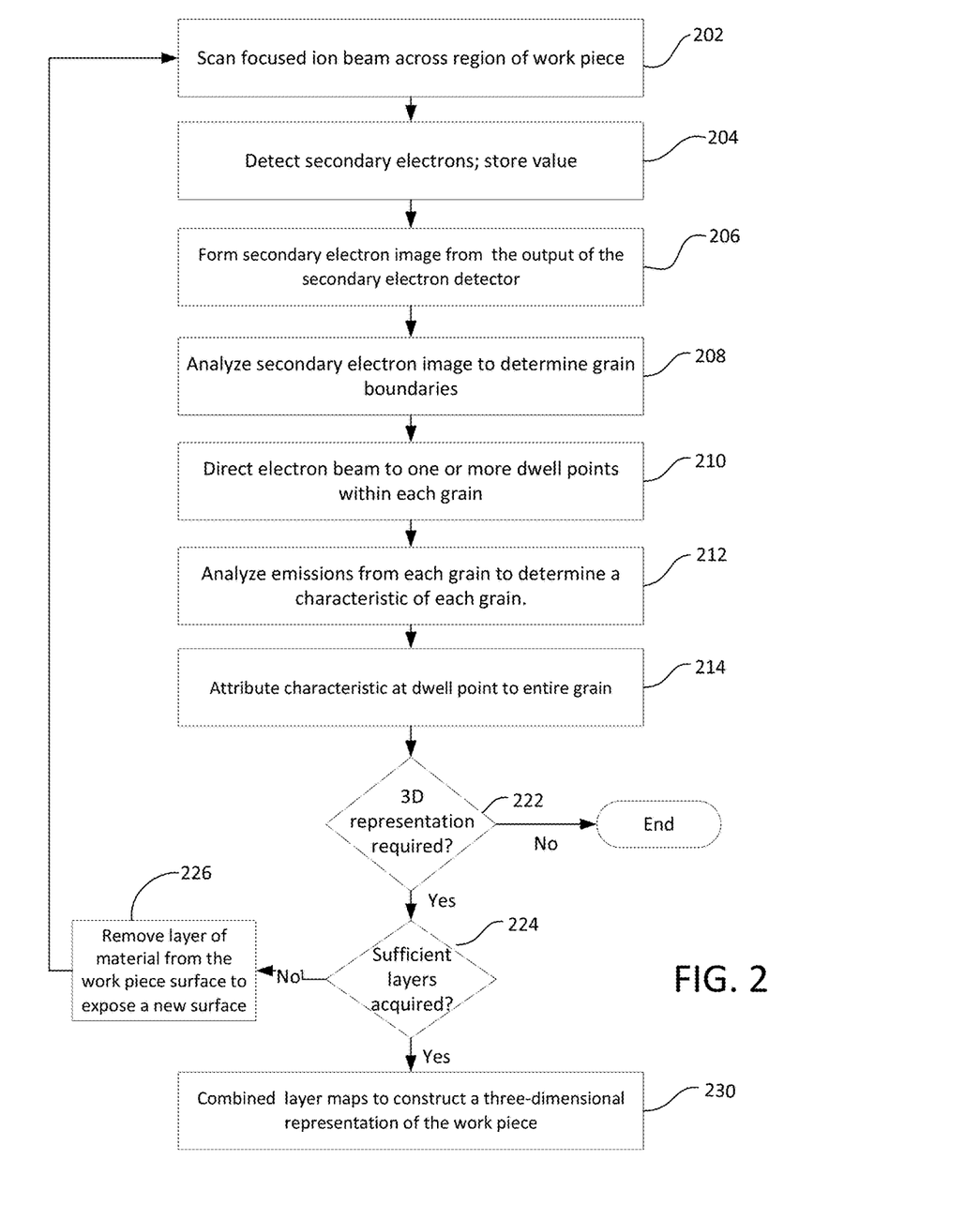
FIG. 2 shows a method of mapping a work piece using an ion channeling image.

FIG. 2 shows the steps of using an ion beam to obtain an ion channeling image and using an electron beam in a method of characterizing a sample. In step 202, a focused ion beam is directed toward a sample surface and scanned over a region of the work piece surface. As used herein, "scanning the work piece" typically means scanning a region of the work piece and does not necessarily require scanning the entire work piece. The ion beam may be moved relative to the sample or the sample may be moved relative to the ion. For example, the ion beam may be moved in a raster pattern, a serpentine pattern, or an arbitrary pattern, including a sparse scan.

In step 204, secondary electrons emitted from the work piece surface are detected by a detector and the gray level, determined by the number of secondary electron detected during each dwell period, is stored for each dwell point. For example, an Everhart-Thornley detector, which comprises a combination of a scintillator and photomultiplier can be used, as well as any of various solid state detectors or a silicon photomultiplier. The secondary electron current is integrated and stored while the ion beam is positioned at a dwell point before the ion beam is moved to the next dwell point in the scan.

The ion beam may be, for example, a gallium ion beam from a liquid metal ion source or an argon, xenon, oxygen, and/or other species beam from a plasma ion source. The landing energy of the ion beam is typically between 100 eV and 30,000 eV and the beam current is typically between 1 pA and 10 µA. The spot size of the beam on the work piece surface is typically between about 1 nm and 5000 nm.

The interaction of the ion beam with the sample produces secondary electron emissions that are used in image formation. The intensity of the secondary electron emission is higher when the collision occurs near the sample surface. The likelihood of a collision at or near the sample surface is decreased along channeling directions, or aligned areas of the crystalline structure of the sample, because the ion beam penetrates further into the sample.

Figure 3:
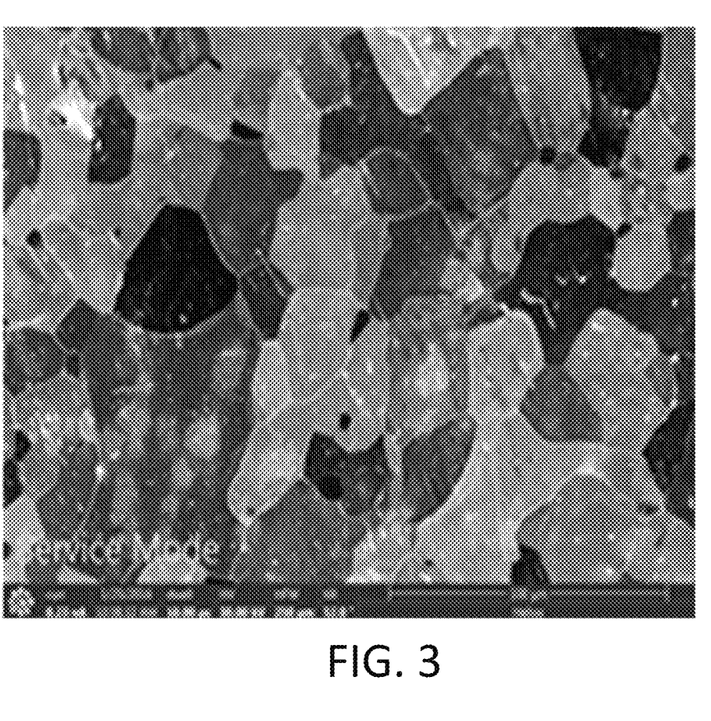
FIG. 3 is an ion channeling image of a work piece containing platinum.
Figure 4A:
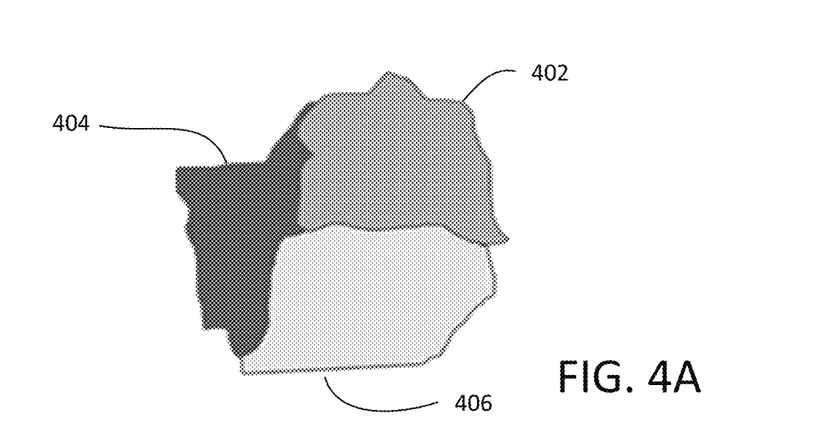
FIG. 4A, FIG. 4B and FIG. 4C illustrate some of the steps of the method of FIG. 2.

In step 206, a high contrast ion channeling image is formed from the output of the secondary electron detector. FIG. 3 shows a high contrast ion channeling image of a platinum sample formed by scanning a gallium ion beam. As can be seen from FIG. 3, individual grains are clearly identifiable. In step 208, the secondary electron images are analyzed to locate changes in contrast within the image, which changes in contrast represent grain boundaries. FIG. 4A shows just a few representative crystal grains to illustrate the process. Grains 402, 404, and 406 have different gray levels and the boundaries between them are therefore discernable by image recognition software or by an operator. Step 208 is preferably performed automatically using computer image processing.

Figure 4B:
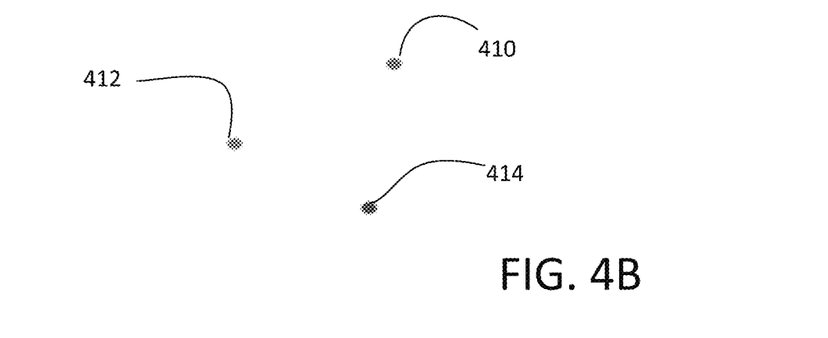

Once individual grains are identified, a charged particle beam, such as an electron beam or an ion beam, is directed to one or more locations within each grain in step 210 and a characteristic of the work piece at each dwell point is determined in step 412. FIG. 4B shows three dwell points, 410, 412, and 414, one dwell point in each crystal grain. The dwell points can be chosen, for example, at the centroid of each grain or dwell points can be chosen randomly or using any other method. The dwell points are preferably well away from the grain boundaries so that the interaction volume of the beam with work piece material does not extend into two grains.

Techniques that can be used to determine a characteristic of the grain include EBSD to determine the crystal structure of the grain, EDS to determine the composition of each grain, or spin indexing to determine the crystal structure and orientation of each grain. An advantage of using spin indexing is that the entire process of defining grain boundaries and analyzing the grains can be performed by an ion beam, which is particularly useful for system lacking an electron beam. Combinations of analysis techniques can be used. For example, EDS can be used to determine the composition at some dwell points, and then when EBSD or spin indexing is used to determine the crystal structure, the determined crystal structure can be compared to the known materials in the work piece as determined by the EDS. EDS could also be performed independently of the grain boundary determination to determine the materials present, for example, by a preliminary scan at points throughout the sample.

Figure 4C:
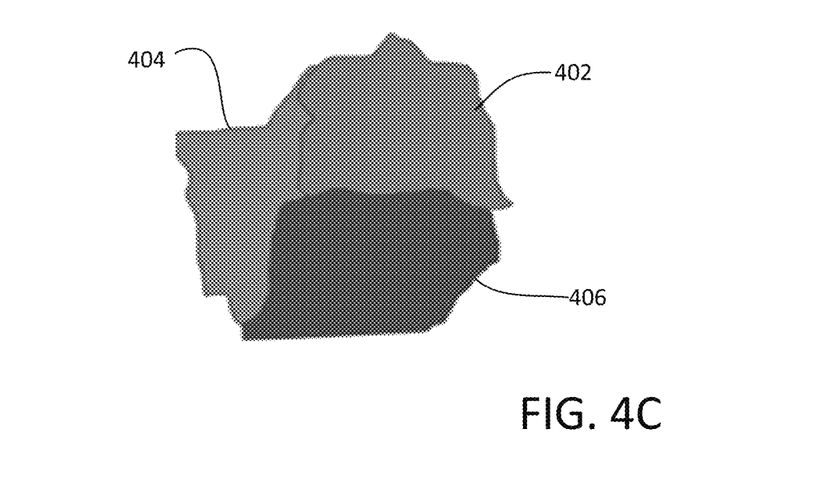

In step 214, the characteristic determined in step 210 attributed to the entire grain to create a map of the work piece as illustrated in FIG. 4C.

In some application, it is desired to create a three-dimensional representation of the work piece by removing a series of layers from the work piece surface to acquire a series of two-dimensional maps, which can be combined to form a three-dimensional representation. In decision block 222, it is determined whether 3-D imaging is desired. If not, then the process ends. If a three-dimensional image is required, then decision block 224 determines whether images of additional surfaces of the work piece need to be measured. If so, then in step 226, a layer of material is removed from the work piece surface to expose a new surface. For example, a layer can be removed using laser processing, such as laser ablation or laser evaporation, focused ion beam processing, or mechanical slicing using a microtome.

After each layer is removed, and the process begins again with steps 202 and the process is repeated until data from sufficient layers are collected. Once sufficient number of layers are collected, a three-dimensional representation of the work piece is compiled from the two dimensional maps.

Figure 5:
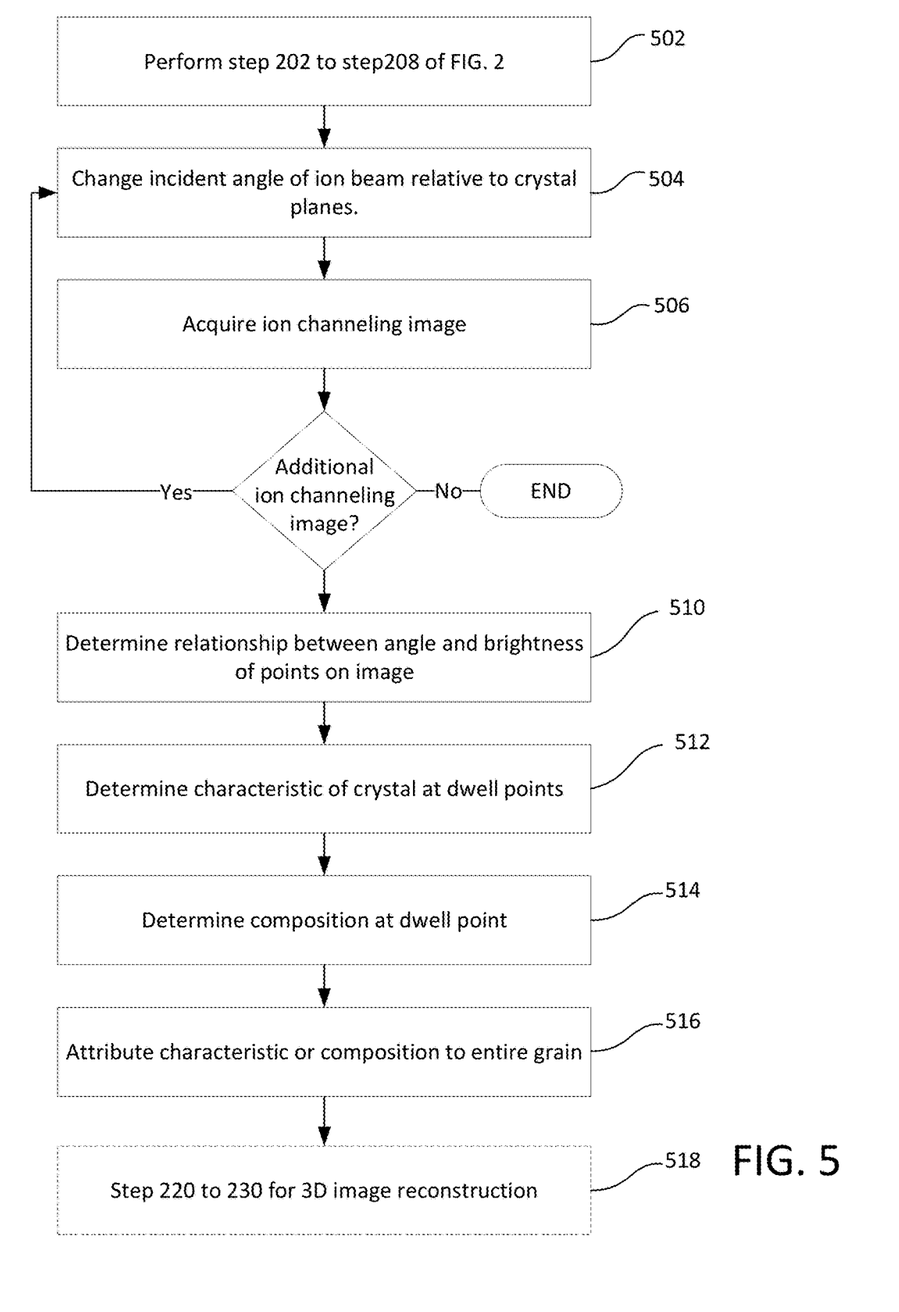
FIG. 5 shows a method of mapping a work piece using an ion channeling image.

FIG. 5 shows another process for analyzing a sample. Steps that are the same as those shown in FIG. 2 are not shown again in FIG. 5. In step 502, steps 202 to 208 of FIG. 2 are performed. In step 504, the angle of the ion beam relative to the crystal planes in the work piece is changed, preferably by a small increment. The angle of the ion beam relative to the crystal planes can be changed by tilting the sample or, if the ion beam is not oriented normal to the sample surface, by rotating the sample. While rotating the sample does not change the angle of incidence of the ion beam relative to the work piece surface, it will change the angle of incidence of the ion beam relative to crystal planes that are not normal to the beam. In many charged particle beam systems, the ion beam is mounted at a non-zero angle from the vertical, sometimes at a 52 degree angle. Many systems include a tilting sample stage, which allows the sample to be tilted relative to the beam.

In step 506, another ion channeling image is acquired of the same region. Because the acquisition of an ion channeling image is rapid compared to the acquisition of an EBSD or EDS, the entire region of the work piece can be scanned with the same dwell point separation, that is, the same resolution, as the original scan in step 202. Alternatively, subsequent scans after the scan of step 202 can be performed with fewer dwell points than the number of dwell points in step 202. For example, if grain boundaries have been determined, a single dwell point in each grain may be sufficient. In another embodiment, every nth dwell point from the original scan can be used, for example, with n=1, 2, 3, 4, etc., as long as at least one dwell point per grain is used.

In decision step 508, it is determined whether the desired number of ion channeling images have been acquired or whether additional ion channeling images are required. In one embodiment, a FIB tilted at 52 degrees, and multiple FIB channeling images are acquired as the sample stage with the work piece is rotated. For example, the work piece may be rotated through three hundred and sixty degrees, with images acquired at two degree increments. That is, 180 ion channeling images are acquired. In another embodiment, the FIB can be oriented normal to the work piece surface to acquire the initial ion channeling image to determine the grain boundaries, and then the work piece can be tilted in, for example, two degree increments. Various combination of tilting and rotating can be used.

If in decision block 508 it is determined that no additional ion channeling images need to be acquired, then in step 510, a relationship between the angle and the brightness of the secondary electron image is determined for each dwell point. As described above, the angle may be tilt angle or rotation angle, depending on the physical arrangement of the system. In step 512, the orientation of the major crystal planes relative to the work piece surface and/or the separation of the major crystal planes is determined from variation of the secondary electron image brightness at each dwell point with rotation or tilt angle. In optional step 514, the composition of each dwell point is determined by matching the crystal structure properties of known materials. In step 516, the characteristic or characteristics determined for a dwell point are attributed to the entire grain that contains the dwell point. Steps 510 to 514 can be performed for every dwell point in the image, for a single dwell point in each crystal grain, or for any number of dwell points. Steps 510 to 514 can be performed quickly because they are computation steps and so do not require beam scans or altering the orientation or position of the sample.

In some embodiments of the process of FIG. 5, step 202 can be skipped, and the grains can be defined by the results of step 512. That is, rather than using an initial scan to define the grain boundaries and then using subsequent scans to characterize the materials within the grain boundaries, the materials at the dwell points can be characterized by spin indexing and the characterizations used to map the work piece and determine the grain boundaries. This can be practical because of the more rapid data acquisition in spin indexing compared to EBSD and EDS.

After a single layer is mapped, optional step 518 shows that additional layers can be mapped to form a three-dimensional representation or reconstruction using a slice-and-view technique as described with respect to FIG. 2, steps 222 to 230.

Figure 6:
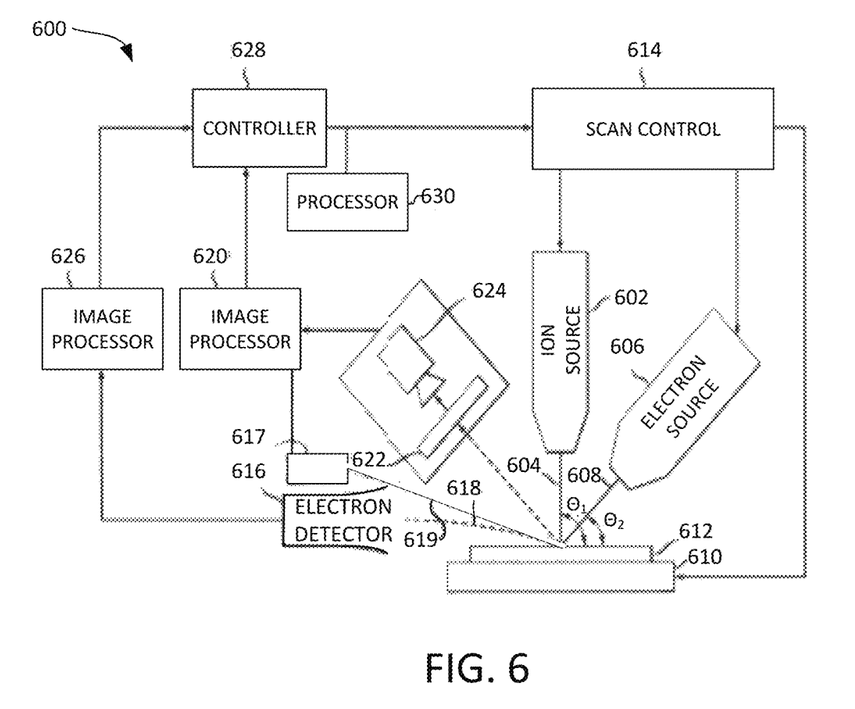
FIG. 6 shows a charged particle beam system suitable for performing the steps of FIGS. 2 and 5.

Referring to FIG. 6, a charged particle beam system 600 includes an ion source 602 for producing an ion beam 604 and an electron source 606 for producing an electron beam 608. A sample stage 610 is provided for holding a sample 612 and is movable along x-y axes to position sample 612 at various locations relative to ion beam 604 and electron beam 608 and along the z-axis to adjust the distance between the sample surface and the charged particle beam columns. Sample stage 610 is also rotatable about a z axis and may be tiltable to orient sample 612 at various angles relative to both beams. Sample 612 is shown at a 90 degree angle relative to ion beam 604. However, sample 612 may be positioned at any selected angle between 0 and 90 degrees. Ion beam 604 is generated by an column 602. A scan control 614 controls relative movement between ion beam 604 and sample 612 and directs ion beam 604 to selected locations on sample 612. Scan control 614 may control movement of ion column 602 relative to sample 612 or may control movement of sample 612 relative to ion column 602, or both. An electron detector 616 is provided to detect secondary electrons 618 that are caused to be emitted from sample 612 by ion beam 604 as it scans across the sample surface. An x-ray detector 617 is provided to detect x-rays 619 emitted from sample 612.

Electron beam 608 is generated by electron column 606. Scan control 614 controls relative movement between electron beam 608 and sample 612. Electron beam 608 is shown at an angle of about 45 degrees relative to sample 612, although other configurations are common. Scan control 614 directs electron beam 608 at spaced apart dwell points on sample 612. Scan control 614 may control movement of electron beam 608 relative to sample 612 or may control movement of sample 612 relative to electron beam 608, or both.

Diffracted backscattered electrons emitted from sample 612 by electron beam 608 form images on a screen 622 which are captured by a charged coupled device (CCD) camera 624 or other low light camera to determine the crystalline structure at a point within a scan area of sample 612. An image processor 620 processes images from camera 624. Another image processor 626 may be provided to process signals from an electron detector 616, which detects secondary electrons emitted from sample 612 upon impact of ion beam 604 or electron beam 608. A controller 628 provides a control signal to scan control 614 to move either ion beam 604 or electron beam 608 relative to sample 612. Data from the sample may be compiled into a table and stored in a computer or processor 630. The data table may have compositional or chemical information for each dwell point on the sample and may be considered an image. This system provides both an ion source 602 and an electron source 606 such that ion beam 604 is used to provide an ion channeling image providing a clear indication of grain boundaries while electron beam 608 is used to determine crystalline structure by using EBSD or EDS.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable. The invention has broad applicability and can provide many benefits as described and shown in the examples above. The embodiments will vary greatly depending upon the specific application, and not every embodiment will provide all the benefits and meet all the objectives that are achievable by the invention.

Embodiments of the disclosure include the above-described system and apparatus configured to carry out the above-described method. Embodiments include, for example, system 600 configured to carry out the methods described herein, and combinations thereof.

Some embodiments provide a method of characterizing a work piece, comprising:

a. scanning an ion beam across an exposed surface of a work piece, the ion beam causing the emission of secondary electrons at multiple imaging points of the scan, the number of secondary electrons emitted varying at different ones of the multiple imaging points;

b. detecting the emitted secondary electrons at each of the multiple imaging point to form an image, the brightness of each point in the image being determined by the number of secondary electrons detected at a corresponding imaging point on the work piece;

c. determining grain boundaries in the work piece using the differences in brightness at different points in the image, the grain boundaries defining multiple grains;

d. directing a charged particle beam toward one or more analysis points within one or more of the grains, the number of the one or more analysis points within each grain being less than the number of imaging points within the same grain;

e. detecting emissions from the work piece sample at each analysis point; and f. determining the composition or crystal structure of one or more grains based on the detected secondary emissions.

Some embodiments further comprise repeatedly removing a layer of material from the work piece surface by laser processing to expose new surfaces on the work piece and repeating the steps a-f on each of the exposed new surfaces.

Some embodiments further comprise reconstructing a three-dimensional image of the work piece using the determine grain boundaries and composition or crystal structure determined from the different exposed surfaces of the work piece.

In some embodiments:

directing a charged particle beam toward one or more analysis points comprises directing an electron beam toward one or more analysis points; and detecting emissions from the work piece at each analysis point comprises forming an electron backscatter diffraction image.

In some embodiments:

directing a charged particle beam toward one or more analysis points comprises directing an electron beam toward one or more analysis points;

detecting emissions from the work piece at each analysis point comprises detecting x-rays; and determining the composition of one or more grains comprises determining the energy of the x-rays.

In some embodiments, determining the energy of the x-rays comprises using energy dispersive x-ray analysis.

In some embodiments:

determining the energy of the x-rays comprises forming an x-ray spectrum; and determining the composition or crystal structure of one or more grains further comprises comparing the x-ray spectrum to reference x-ray spectra of known materials.

In some embodiments determining the composition or crystal structure of one or more grains further comprises comparing the relative number of x-rays in specific frequency channels with the relative number of x-rays in those frequency channels for known materials.

In some embodiments:

directing a charged particle beam toward one or more analysis points comprises directing an ion beam toward one or more analysis points;

detecting emissions from the work piece at each analysis point comprises detecting emissions from the work piece at a first orientation and detecting emissions from the work piece at a second orientation; and determining the composition or crystal structure of one or more grains based on the detected secondary emissions comprises determining the crystal structure by comparing the emissions from the same grain at the different orientations.

In some embodiments:

directing an ion beam toward one or more analysis points comprises directing an ion beam toward the one or more analysis points at a non-normal angle to the work piece surface; and detecting emissions from the work piece at a second orientation comprises rotating the work piece about an axis normal to the work piece surface before detecting the emissions.

In some embodiments, the grains are composed of crystals characterized by crystal planes and directing a charged particle beam toward one or more analysis points comprises directing an ion beam toward one or more analysis points;

detecting emissions from the work piece at each analysis point comprises detecting emissions from each analysis point with the ion beam oriented at different angles to the crystal planes to define a relationship between the emissions and the orientation angle; and determining the composition or crystal structure of one or more grains based on the detected secondary emissions comprises determining the crystal structure from the relationship between the emissions and the orientation angle.

Embodiments of the invention provide a method of characterizing a work piece having crystal grains, the crystal grains having crystal planes having a crystal plane orientation, comprising:

scanning an ion beam across a region of the work piece to determine grain boundaries, the region including multiple crystal grains and the ion beam causing the emission of secondary electrons at multiple imaging points of the scan, the number of secondary electrons emitted at each point of the scan varying with the angle between the ion beam and the crystal planes;

detecting the emitted secondary electrons to form an image, the brightness of each point in the image being determined by the number of secondary electrons detected at a corresponding point on the work piece;

determining grain boundaries in the work piece using the differences in brightness at different points in the image, the grain boundaries defining multiple grains;

acquiring multiple secondary electron images by scanning the ion beam across the region of the work piece multiple times at different angle between the crystal planes and the ion beam;

comparing the secondary electron images at the different angles to determine characteristics of the crystal planes; and comparing the characteristics of the crystal planes to reference characteristics of crystal planes of known materials to determine the composition of the grain.

In some embodiments, acquiring multiple secondary electron images by scanning the ion beam across the region of the work piece multiple times comprises scanning fewer points than were scanned to determine grain boundaries.

In some embodiments, acquiring multiple secondary electron images by scanning the ion beam across the region of the work piece multiple times at different angle comprises:

scanning the ion beam at a non-normal angle to the work piece surface; and rotating the work piece about an axis normal to the work piece surface before detecting the emissions.

In some embodiments:

comparing the secondary electron images at the different angles to determine characteristics of the crystal planes comprises determining a relationship between the emissions and the orientation angle; and comparing the characteristics of the crystal planes to reference characteristics of crystal planes of known materials comprises determining the composition or crystal structure of one or more grains based on the detected secondary emissions comprises determining the crystal structure from the relationship between the emissions and the orientation angle.

Some embodiments provide a charged particle beam system, comprising;

an ion optical source for producing an ion to be directed at a sample;

an ion optical column for forming an ion beam from the ions and for focusing and positioning the ion beam on the sample surface;

a first detector for detecting a first type of emissions from the sample caused by impingement of the ion beam;

a source for producing electrons to be directed at the sample;

an electron optical column for forming an electron beam, focusing the electron beam onto the work piece, and positioning the electron beam on the work piece;

a second detector for detecting a second type of emissions from the sample caused by impingement of the electron beam; and a system controller including a program memory storing machine readable instructions for performing any of the methods described herein.

It should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a non-transitory storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of non-transitory computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

The terms "work piece," "sample," "substrate," and "specimen" are used interchangeably in this application unless otherwise indicated. Further, whenever the terms "automatic," "automated," or similar terms are used herein, those terms will be understood to include manual initiation of the automatic or automated process or step.

In the following discussion and in the claims, the terms "including" and "comprising" are used in an open-ended fashion, and thus should be interpreted to mean "including, but not limited to . . . " To the extent that any term is not specially defined in this specification, the intent is that the term is to be given its plain and ordinary meaning. The accompanying drawings are intended to aid in understanding the present invention and, unless otherwise indicated, are not drawn to scale. Particle beam systems suitable for carrying out the present invention are commercially available, for example, from FEI Company, the assignee of the present application.

The various features described herein may be used in any functional combination or sub-combination, and not merely those combinations described in the embodiments herein. As such, this disclosure should be interpreted as providing written description of any such combination or sub-combination.

"Imaging" as used herein is not limited to a visual display of the sample or to information displayed in an observable manner Data from the sample may be collected and stored in a computer for analysis without displaying the data in the form of an image. The data may be stored in a table that includes crystal orientation, crystal structure, or compositional for each dwell point on the sample and may be considered an image or a map. An image may also be a visual appearance of the sample on a display. Data that represents a three-dimensional reconstruction of the sample is also considered an image.

Although the present invention and its advantages have been described in detail, it should be understood that various changes, substitutions and alterations can be made to the embodiments described herein without departing from the scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of characterizing a work piece, comprising:
   a. scanning an ion beam across an exposed surface of a work piece, the ion beam causing the emission of secondary electrons at multiple imaging points of the scan, the number of secondary electrons emitted varying at different ones of the multiple imaging points;
   b. detecting the emitted secondary electrons at each of the multiple imaging point to form an image, the brightness of each point in the image being determined by the number of secondary electrons detected at a corresponding imaging point on the work piece;
   c. determining grain boundaries in the work piece using the differences in brightness at different points in the image, the grain boundaries defining multiple grains;
   d. directing a charged particle beam toward one or more analysis points within one or more of the grains, the number of the one or more analysis points within each grain being less than the number of imaging points within the same grain;
   e. detecting secondary emissions from the work piece at each analysis point; and
   f. determining the composition or crystal structure of one or more grains based on the detected secondary emissions.

2. The method of claim 1 further comprising repeatedly removing a layer of material from the work piece surface by laser processing to expose new surfaces on the work piece and repeating the steps a-f on each of the exposed new surfaces.

3. The method of claim 2 further comprising reconstructing a three-dimensional image of the work piece using the determine grain boundaries and composition or crystal structure determined from the different exposed surfaces of the work piece.

4. The method of claim 1 in which:
   directing a charged particle beam toward one or more analysis points comprises directing an electron beam toward one or more analysis points; and
   detecting secondary emissions from the work piece at each analysis point comprises forming an electron backscatter diffraction image.

5. The method of claim 1 in which:
   directing a charged particle beam toward one or more analysis points comprises directing an electron beam toward one or more analysis points;
   detecting secondary emissions from the work piece at each analysis point comprises detecting x-rays; and
   determining the composition of one or more grains comprises determining the energy of the x-rays.

6. The method of claim 5 in which determining the energy of the x-rays comprises using energy dispersive x-ray analysis.

7. The method of claim 6 in which:
   directing an ion beam toward one or more analysis points comprises directing an ion beam toward the one or more analysis points at a non-normal angle to the work piece surface; and
   detecting secondary emissions from the work piece at a second orientation comprises rotating the work piece about an axis normal to the work piece surface before detecting the secondary emissions.

8. The method of claim 5 in which
   determining the energy of the x-rays comprises forming an x-ray spectrum; and
   determining the composition or crystal structure of one or more grains further comprises comparing the x-ray spectrum to reference x-ray spectra of known materials.

9. The method of claim 5 in which determining the composition or crystal structure of one or more grains further comprises comparing the relative number of x-rays in specific frequency channels with the relative number of x-rays in those frequency channels for known materials.

10. The method of claim 1 in which:
    directing a charged particle beam toward one or more analysis points comprises directing an ion beam toward one or more analysis points;
    detecting secondary emissions from the work piece at each analysis point comprises detecting secondary emissions from the work piece at a first orientation and detecting secondary emissions from the work piece at a second orientation; and
    determining the composition or crystal structure of one or more grains based on the detected secondary emissions comprises determining the crystal structure by comparing the secondary emissions from the same grain at the different orientations.

11. The method of claim 1 in which the grains are composed of crystals characterized by crystal planes:
    directing a charged particle beam toward one or more analysis points comprises directing an ion beam toward one or more analysis points;
    detecting secondary emissions from the work piece at each analysis point comprises detecting secondary emissions from each analysis point with the ion beam oriented at different angles to the crystal planes to define a relationship between the secondary emissions and the orientation angle; and
    determining the composition or crystal structure of one or more grains based on the detected secondary emissions comprises determining the crystal structure from the relationship between the secondary emissions and the orientation angle.

12. A charged particle beam system, comprising;
    an ion optical source for producing an ion to be directed at a sample;
    an ion optical column for forming an ion beam from the ions and for focusing and positioning the ion beam on the sample surface;
    a first detector for detecting a first type of emissions from the sample caused by impingement of the ion beam;
    a source for producing electrons to be directed at the sample;
    an electron optical column for forming an electron beam, focusing the electron beam onto the sample, and positioning the electron beam on the sample;
    a second detector for detecting a second type of emissions from the sample caused by impingement of the electron beam; and
    a system controller including a program memory storing machine readable instructions for performing the method of claim 1.

13. A method of characterizing a work piece having crystal grains, the crystal grains having crystal planes having a crystal plane orientation, comprising:
    scanning an ion beam across a region of the work piece to determine grain boundaries, the region including multiple crystal grains and the ion beam causing the emission of secondary electrons at multiple imaging points of the scan, the number of secondary electrons emitted at each point of the scan varying with the angle between the ion beam and the crystal planes;

detecting the emitted secondary electrons to form an image, the brightness of each point in the image being determined by the number of secondary electrons detected at a corresponding point on the work piece;

determining grain boundaries in the work piece using the differences in brightness at different points in the image, the grain boundaries defining multiple grains;

acquiring multiple secondary electron images by scanning the ion beam across the region of the work piece multiple times at different angles between the crystal planes and the ion beam while detecting secondary electron emissions;

comparing the secondary electron images at the different angles to determine characteristics of the crystal planes; and comparing the characteristics of the crystal planes to reference characteristics of crystal planes of known materials to determine the composition of the crystal grains.

14. The method of claim 13 in which acquiring multiple secondary electron images by scanning the ion beam across the region of the work piece multiple times comprises scanning fewer points than were scanned to determine grain boundaries.

15. The method of claim 13 in which acquiring multiple secondary electron images by scanning the ion beam across the region of the work piece multiple times at different angles comprises:

scanning the ion beam at a non-normal angle to the work piece surface; and rotating the work piece about an axis normal to the work piece surface before detecting the secondary electron emissions.

16. The method of claim 13 in which:

comparing the secondary electron images at the different angles to determine characteristics of the crystal planes comprises determining a relationship between the secondary electron emissions and the orientation angle; and comparing the characteristics of the crystal planes to reference characteristics of crystal planes of known materials comprises determining the crystal structure from the relationship between the secondary electron emissions and the orientation angle.

* * * * *